United States Patent [19]

Gaffney et al.

[11] Patent Number: 5,136,108
[45] Date of Patent: Aug. 4, 1992

[54] PRODUCTION OF OXYGENATED FUEL COMPONENTS

[75] Inventors: Anne M. Gaffney, West Chester; William J. Piel, Media, both of Pa.

[73] Assignee: Arco Chemical Technology, L.P., Wilmington, Del.

[21] Appl. No.: 759,252

[22] Filed: Sep. 13, 1991

[51] Int. Cl.$^5$ ............................................. C07C 41/06
[52] U.S. Cl. ................................................... 568/697
[58] Field of Search ....................................... 568/697

[56] References Cited

U.S. PATENT DOCUMENTS

| | | | |
|---|---|---|---|
| 4,500,651 | 2/1985 | Lok et al. | 502/208 |
| 4,575,566 | 3/1986 | Vora | 568/697 |
| 4,605,787 | 8/1986 | Chu et al. | 568/697 |
| 4,683,217 | 7/1987 | Lok et al. | 502/214 |
| 4,814,519 | 3/1989 | Harandi et al. | 568/697 |
| 4,826,507 | 5/1989 | Harandi et al. | 44/77 |
| 4,827,045 | 5/1989 | Harandi et al. | 568/697 |
| 4,830,635 | 5/1989 | Harandi et al. | 44/56 |
| 4,835,329 | 5/1989 | Harandi et al. | 585/415 |
| 4,854,939 | 8/1989 | Harandi et al. | 44/77 |
| 4,857,667 | 8/1989 | Harandi et al. | 585/403 |
| 4,882,038 | 11/1989 | Lok et al. | 208/111 |
| 4,925,455 | 5/1990 | Harandi et al. | 44/77 |
| 4,957,709 | 9/1990 | Harandi | 422/134 |
| 4,962,239 | 10/1990 | Bell et al. | 568/697 |
| 4,967,020 | 10/1990 | Marler et al. | 568/896 |
| 4,969,987 | 11/1990 | Le et al. | 203/67 |
| 4,973,460 | 11/1990 | Flanigen et al. | 423/306 |
| 4,988,366 | 1/1991 | Harandi et al. | 44/449 |
| 5,001,292 | 3/1991 | Harandi et al. | 585/322 |
| 5,003,112 | 3/1991 | Knifton | 568/697 |
| 5,004,858 | 4/1991 | Gajda | 585/667 |
| 5,009,859 | 4/1991 | Harandi et al. | 422/189 |
| 5,013,329 | 5/1991 | Bell et al. | 44/448 |
| 5,015,782 | 5/1991 | Harandi et al. | 568/697 |
| 5,015,783 | 5/1991 | Vora et al. | 568/697 |
| 5,024,679 | 6/1991 | Harandi et al. | 44/449 |
| 5,026,529 | 6/1991 | Harandi et al. | 422/190 |

FOREIGN PATENT DOCUMENTS 0026041 1/1981 European Pat. Off. .

Primary Examiner—Marianne M. Cintins
Assistant Examiner—Michael B. Hydorn
Attorney, Agent, or Firm—William C. Long

[57] ABSTRACT

A low value $C_5$ feedstock is efficiently upgraded by a series of process steps involving reacting branched tertiary olefins in the feed and from subsequent isomerization with methanol and/or water to form TAME and/or TAA, separating isopentene by distillation from the reaction mixture, separating product TAME and/or TAA by distillation from linear $C_5$ hydrocarbons, and converting the linear $C_5$ hydrocarbons by skeletal isomerization to branched $C_5$ hydrocarbons which are recycled to said reaction with methanol and/or water.

2 Claims, 1 Drawing Sheet

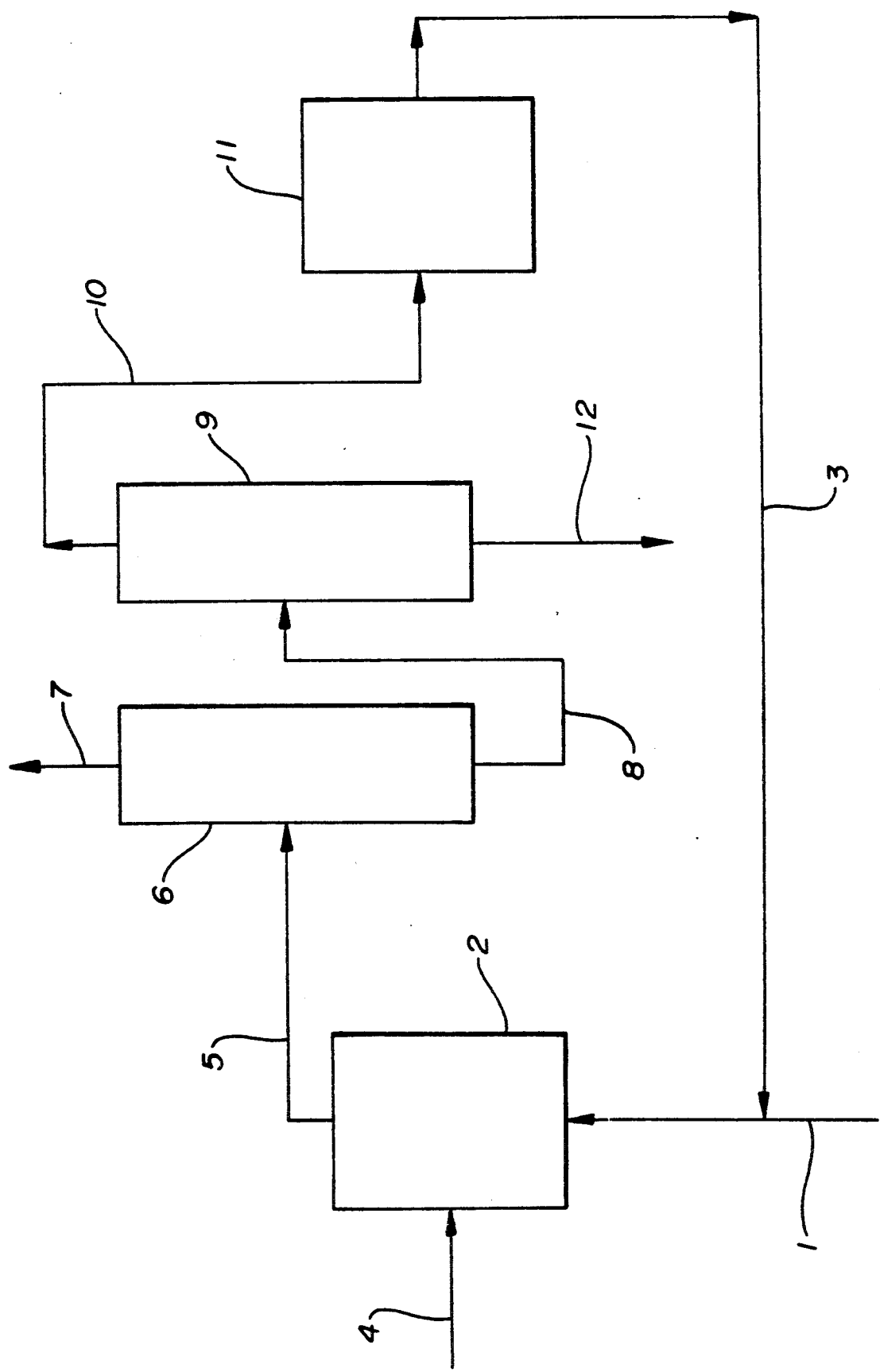

PRODUCTION OF OXYGENATED FUEL COMPONENTS

BACKGROUND OF THE INVENTION

1. Field of the Invention

The present invention relates to the improved production or yield of tertiary amyl methyl ether (TAME) and/or tertiary amyl alcohol (TAA) from predominantly $C_5$ hydrocarbon feed streams containing mixed $C_5$ olefins which are of relatively low value.

2. Description of Prior Art

Various methods are known in the art for the conversion of branched olefins to the corresponding ether and/or alcohol. See U.S. Pat. Nos. 4,605,787, 4,575,566, 4,925,455, 4,957,709, 4,962,239, 4,967,020, 4,969,987, 4,830,685, 4,835,329, 4,827,045, 4,826,507, 4,814,519, 5,001,292, 5,003,112 and the like.

Likewise, methods are known whereby linear olefins can be converted by skeletal isomerization to branched olefins See, for example, U.S. Pat. Nos. 4,037,029, 4,793,984, 4,683,217, 4,973,785, 4,882,038, 4,758,419, 4,500,651, 4,973,460 and the like.

Various integrated processes for the conversion of hydrocarbons to gasoline components which involve etherification of branched tertiary $C_4$ and/or $C_5$ olefins are also known. See, for example, U.S. Pat. Nos. 4,988,366, 4,925,455, 4,957,709, 4,969,987, 4,830,635, 4,835,329, 4,827,045, 4,826,507, 4,854,939, 5,001,292, 4,857,667, 5,009,859, 5,015,782, 5,013,329 and the like.

European publication 0 026,041 describes a process for producing olefins and/or ethers of high octane number from a wide $C_2$ to $C_{10}$ olefinic stream. The wide olefinic feedstock is restructured over a zeolite catalyst to form primarily $C_4$ to $C_7$ olefins, the $C_4$ to $C_7$ iso-olefins are reacted with methanol to form high octane ethers and unreacted olefins and methanol are separated from the ether product and recycled to the restructuring operation.

U.S. Pat. No. 4,814,519 shows a two-stage process for the production of ethers from olefin-containing feedstock such as from an FCC unit whereby the feedstock is reacted under conditions to maximize production of $C_4$-$C_5$ iso-olefins, particularly tertiary iso-olefins. The resulting iso-olefin rich product is then subjected to a catalytic etherification reaction to produce ethers such as TAME.

The above art teaches that the amount of ether which can be produced from a mixed olefin stream is limited to the contained branched olefins and that the amount of contained branched olefins in the stream is limited by the thermodynamic equilibrium condition of this source olefin stream.

The current invention provides a process whereby substantially all of the contained olefin in the feed stream can be upgraded to TAME.

BRIEF DESCRIPTION OF THE INVENTION

In accordance with the present invention, a hydrocarbon stream comprised predominantly of $C_5$ hydrocarbons including both olefins and paraffins such as is produced by FCC procedures is reacted in a first step with lower alcohol and/or water under conditions such that the branched tertiary $C_5$ olefins contained in the feed selectively react to form the ether and/or alcohol, e.g. TAME and/or TAA. The resulting reaction mixture is fractionally distilled in order to separate a lower boiling isopentane fraction from a mixture of linear $C_5$ olefins and paraffin and TAME and/or TAA, the isopentane fraction being separated and representing a valuable gasoline blending fraction. The mixture of linear $C_5$'s and TAME and/or TAA is separated by fractional distillation and a product fraction of TAME and/or TAA is recovered. The linear $C_5$ stream is passed to an isomerization reactor wherein skeletal isomerization takes place, converting normal $C_5$ olefins to branched tertiary $C_5$ olefins and converting pentane to isopentane. The isomerizate product stream is then recycled to the first reaction zone and the branched tertiary olefins from the isomerization step together with net feed branched $C_5$ olefins are converted to TAME and/or TAA. Subsequently, isopentane from the isomerization is separated together with the net isopentane feed.

DESCRIPTION OF THE DRAWINGS

The accompanying drawing illustrates in schematic form practice of the invention.

DETAILED DESCRIPTION OF THE INVENTION

Referring to the accompanying drawing, a mixed $C_5$ hydrocarbon feed stream such as that from an FCC unit and containing $C_5$ olefins and paraffins is introduced via line 1 into zone 2. The hydrocarbon feed stream comprises at least 90% by volume $C_5$ hydrocarbons of which at least 40% by volume are olefins. Of the olefins, at least 40% are tertiary olefins. A recycle stream from the isomerization step is also introduced into zone 2 via line 3. Lower alcohol such as methanol and/or water is introduced into zone 2 via line 4.

In zone 2, branched tertiary $C_5$ olefins are selectively reacted with the lower alkanol and/or water in accordance with known procedures to form ether such as TAME and/or TAA.

The reaction mixture passes via line 5 from zone 2 to distillation zone 6 wherein an isopentane stream is separated overhead via line 7 as a low boiling fraction which is useful as a gasoline blending material. This separation is conveniently accomplished at this point in the process since the branched olefins which normally are extremely difficult to separate from isopentane because of the closeness of the boiling points, have been converted to the much higher boiling ether and/or alcohol.

From zone 6 the higher boiling liquid fraction comprised of the ether and/or alcohol formed in zone 2 and linear $C_5$ olefins and paraffin pass via line 8 to distillation zone 9. In zone 9 the linear olefins and paraffins are separated as a light overhead fraction via line 10 and pass to isomerization zone 11.

The product TAME and/or TAA stream passes from zone 9 via line 12 and comprises a useful and valuable product of the invention which can be used, for example, as an octane enhancing gasoline component.

In isomerization zone 11, the linear $C_5$ olefins and paraffin are converted by known skeletal isomerization fixed reactor bed procedures to branched tertiary $C_5$ olefins and isopentane. Generally, the conversion in zone 11 is carried out such that close to the thermodynamic equilibrium mixture is obtained at the selected reaction conditions. Under the isomerization conditions, considerable isomerization of the linear $C_5$ paraffin to the higher octane value branched $C_5$ paraffins takes place which is an additional advantage of the invention.

The isomerization reaction mixture from zone 11 passes via line 3 to zone 2 wherein the branched C₅ olefins formed in zone 11 are selectively converted to the ether and/or alcohol as previously described.

Practice of the invention has the outstanding advantage that a low value material such as the C₅ olefin and paraffin mixture from an FCC unit can be employed as feedstock. The olefin content of the feed material can be essentially completely converted to the valuable ether and/or alcohol gasoline blending components. In addition, the separation of C₅ branched paraffins is readily accomplished after the branched olefins first are converted to ether and/or alcohol. An added benefit is the conversion of linear C₅ paraffins to higher octane branched C₅ paraffins.

Statutory regulations are expected to require in the near future a lowering of both the olefin content of gasoline and the amount of components boiling over 200° F. In accordance with the invention, relatively low value olefins are converted to TAME thus facilitating compliance with such regulations while producing a higher quality end product.

Both the etherification reaction in zone 2 and the skeletal isomerization in zone 11 are carried out in accordance with known procedures as taught, for example, in the patents listed above.

Particular preferred catalysts for use in the skeletal isomerization are the medium pore-sized molecular sieves such as SAPO-11 and SAPO-31 and molecular sieves having the same general pore configuration. Especially preferred are the molecular sieves which are described in U.S. Pat. Nos. 4,973,785 and 4,793,984 and which contain in addition to the framework oxide units of AlO₂, SiO₂ and PO₂ an oxide of a metal from the group consisting of arsenic, barium, boron, chromium, cobalt, gallium, germanium, iron, lithium, magnesium, manganese, titanium, vanadium and zinc. Suitable catalysts employed are the MgAPSO-11 and 31 sieves described in U.S. Pat. No. 4,882,038 and 4,758,419.

The skeletal isomerization is carried out at elevated temperatures, i.e., above 300° C.

It is preferred that the vapor phase isomerization reaction temperature be maintained in excess of 900° F., and preferably in excess of 925° F. Generally, the temperature should not exceed 1350° F. Normal isomerization pressures ranging from about atmospheric to 1,000 psig are conveniently employed. Isomerization space velocities of the order of about 1 to about 10,000 hr.$^{-1}$ WHSV are employed, preferably 10 to 1000 hr.$^{-1}$ WHSV.

The isomerization vapor feed can contain, in addition to the hydrocarbon to be isomerized, inert gas and/or steam, although the use of these materials is not necessary or preferred.

The reaction of methanol with isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, Dec. 1977. An article entitled "MTBE and TAME—A Good Octane Boosting Combo," by J. D. Chase, et al., *The Oil and Gas Journal*, Apr. 9, 1979, pages 149-152, discusses the technology. A preferred catalyst is a polymeric sulfonic acid exchange resin such as Amberlyst 15.

In the etherification process it is known that alkanol and iso-olefins may be reacted in equimolar quantities or either reactant may be in molar excess to influence the complete conversion of the other reactant. Because etherification is an incomplete reaction, the etherification effluent comprises unreacted alkanol and unreacted hydrocarbons. On a stoichiometric equivalencies basis, equimolar quantities of methanol and iso-olefins are advantageous, but an excess between 2 and 200% of either component can be passed to the etherification reaction unit. In the present invention, the molar ratio of alkanol to iso-olefin can be between 0.7 and 2.

The following example illustrates the invention.

A C₅ hydrocarbon feed mixture from an FCC unit was fed at the rate of 100 M lbs./hr. to reaction zone 2 via line 1. The feed mixture had the following composition by volume:

| | |
|---|---|
| 3-methyl butene-1 | 1.3% |
| isopentane | 50.0% |
| Pentene-1 | 3.5% |
| 2-methyl butene-1 | 8.8% |
| n-pentane | 6.0% |
| trans pentene-2 | 9.7% |
| cis pentene-2 | 4.8% |
| 2-methyl butene-2 | 15.9% |

A recycle stream from isomerization zone 11 was returned via line 3 at the rate of 55 M lbs./hr and was introduced into zone 2 along with the fresh feed. The recycle stream had the following composition by volume:

| | |
|---|---|
| Isopentane | 17.0% |
| Pentene-1 | 0.8% |
| 2-methyl butene-1 | 18.5% |
| n-pentane | 9.2% |
| trans-pentene-2 | 6.6% |
| cis-pentene-2 | 3.7% |
| 2-methyl butene-2 | 44.3% |

Methanol in amount of 19.5 M lbs./hr. was introduced into zone 2 by means of line 4.

In zone 2, the reaction of methanol with branched tertiary C₅ olefins was carried out at 70° C. and 60 psig using a sulfonic acid ion exchange catalyst. Conversion of the tertiary C₅ olefins to TAME was 70%. The reaction mixture from zone 2 was passed via line 5 and fractionally distilled in distillation zone 6. The reaction mixture from zone 2 had the following composition by volume:

| | |
|---|---|
| Isopentane | 34.0% |
| Pentene-1 | 2.2% |
| 2-methyl butene-1 | 2.1% |
| n-pentane | 6.3% |
| trans-pentene-2 | 7.7% |
| cis-pentene-2 | 3.9% |
| 2-methyl butene-2 | 8.3% |
| tertiary amyl methyl ether | 35.5% |

Distillation zone 6 comprised 25 theoretical stages and an overhead isopentane stream was removed via line 7 at the rate of 57.7 m lbs./hr. The isopentane stream had the following composition by volume:

| | |
|---|---|
| Isopentane | 97.1% |
| Pentene-1 | 2.9% |

Conditions of distillation were an overhead temperature of 50° C. and pressure of 20 psig.

A bottoms stream at 65° C. was removed from zone 6 and passed via line 8 to fractional distillation zone 9 which comprised 20 theoretical stages. An overhead fraction was removed at 60° C. and 20 psig via line 10 and was passed to isomerization zone 11. This overhead fraction had the following composition by volume:

| | | |
|---|---|---|
| Isopentane | 6.1% | |
| Pentene-1 | 4.1% | |
| 2-methyl butene-1 | 6.6% | |
| n-pentane | 20.1% | |
| trans-pentene-2 | 24.3% | |
| cis-pentene-2 | 12.4% | |
| 2-methyl butene-2 | 26.4% | |

A product TAME stream was removed from zone 9 at 105° C. at the rate of 61.8 M lbs./hr and was recovered as a valuable oxygenated gasoline component product.

The overhead stream from distillation column 9 was subjected to skeletal isomerization in isomerization zone 11; the conditions of isomerization were a space velocity of $2^{-hr.}$, a temperature of 210° C. and a pressure of 600 psig. A catalyst comprised of 3% P in ZSM-5 was used to accomplish the skeletal isomerization. From zone 11, the isomerization product mixture passed at the rate of 55 M lbs./hr. via line 3 to reaction zone 2.

What is claimed is:

1. The process for producing TAME and/or TAA gasoline blending components from a feedstock comprised of at least 90 vol. % $C_5$ hydrocarbons of which at least 40 vol. % are olefins, said olefins being comprised of at least 40% tertiary olefins, which comprises:
    a) reacting tertiary $C_5$ olefins in said feedstock with methanol, water, or a mixture of methanol and water to form respectively TAME, TAA, or a mixture of TAME and TAA gasoline blending components;
    b) distilling the reaction mixture from step a) to separate and recover an isopentane stream from a heavier stream comprising said TAME, TAA, or a mixture of TAME and TAA and linear $C_5$ olefins and paraffin;
    c) distilling the heavier stream from step b) to separate product TAME, TAA, or a mixture of TAME and TAA gasoline blending components from a linear $C_5$ hydrocarbon stream;
    d) converting linear $C_5$ hydrocarbons from step c) by skeletal isomerization to branched $C_5$ hydrocarbons; and
    e) recycling the branched $C_5$ hydrocarbons from step d) to step a).

2. The process of claim 1 wherein said feedstock is reacted with methanol and TAME is formed in step a).

* * * * *